United States Patent [19]

DeFusco, Jr. et al.

[11] 4,434,304
[45] Feb. 28, 1984

[54] SYNTHESIS OF TRINITROPHLOROGLUCINOL

[75] Inventors: Albert A. DeFusco, Jr.; Arnold T. Nielsen; Ronald L. Atkins, all of Ridgecrest, Calif.

[73] Assignee: The United States of America as represented by the Secretary of the Navy, Washington, D.C.

[21] Appl. No.: 434,460

[22] Filed: Oct. 15, 1982

[51] Int. Cl.$^3$ .............................................. C07C 79/30
[52] U.S. Cl. .................................... 568/710; 568/711; 568/712
[58] Field of Search ........................ 568/710, 711, 712

[56] References Cited

U.S. PATENT DOCUMENTS

| | | | |
|---|---|---|---|
| 2,256,195 | 9/1941 | Bilbert | 568/711 |
| 2,301,912 | 11/1942 | Jones et al. | 568/710 |
| 2,311,283 | 2/1943 | Roblin | 568/710 |
| 2,810,767 | 10/1957 | Clarke et al. | 568/711 |
| 2,945,890 | 7/1960 | Allan | 568/711 |

FOREIGN PATENT DOCUMENTS 126368  5/1919  United Kingdom ................ 568/710

OTHER PUBLICATIONS

Huntress "Identification of Pure Organic Compounds" p. 248, John Wiley & Sons, New York, NY (1941).
Salter et al., Chem. Abst., vol. 73, 76860h (1970).
Sharnin et al., Chem. Abst., vol. 85, 108416; (1976).
Travagli, Chem. Abst., vol. 45, 7544 (1951).
Sorm et al., Chem. Abst., vol. 31, 8520 (1937).
Flürscheim et al., J. Chem. Soc., 304 (1928).
Freudenburg et al., Ann., vol. 442, 309 (1925).
Hertel et al., Chem. Abst., vol. 25, 2893 (1931).

*Primary Examiner*—Werren B. Lone
*Attorney, Agent, or Firm*—R. F. Beers; W. Thom Skeer; Bruce H. Cottrell

[57] ABSTRACT

A one pot process for the preparation of trinitrophloroglucinol by the addition of a nitric acid and sulfuric acid mixture to phloroglucinol in sulfuric acid where the nitric acid and phloroglucinol are present in stoichiometric amounts.

4 Claims, No Drawings

4,434,304

SYNTHESIS OF TRINITROPHLOROGLUCINOL

BACKGROUND OF THE INVENTION

1. Field of the Invention

This invention relates to an improved method of preparing trinitrophloroglucinol.

2. Description of the Prior Art

Many aromatic compounds with nitro groups on the rings are useful explosives. Trinitrophloroglucinol can serve as an explosive, but this use has been limited by the lack of a safe, simple, and inexpensive method of production. Salts of trinitrophloroglucinol are useful as initiators. Additionally, trinitrophloroglucinol serves as an important intermediate in the synthesis of several other explosives.

Previously, trinitrophloroglucinol has been obtained in a variety of ways. Typical procedures include the alkaline hydrolysis of precursors such as pentanitroaniline (B. Flürscheim et al., J. Chem. Soc., 3044, 1928) or 1,3,5-trichloro-2,4,6-trinitrobenzene (F. Sorm et al., Chem. Obzor., 12, 153, 1937; Chem. Zentralblatt, II, 4033, 1937). Another procedure involving nitrolysis of the tripotassium salt of trinitrosophloroglucinol is quite hazardous (K. Freudenberg et al., Ann. 442, 309, 1925). Other methods begin with phloroglucinol and involve the nitrosation of the phenol, followed by subsequent oxidation with nitric acid to give the trinitrophloroglucinol as shown in Ger. Pat. No. 1,959,930 or the two-step nitration of Russ. Pat. No. 515,740 which nitrated the phloroglucinol to give them mononitro phloroglucinol, followed by a second nitration to give the trinitrophloroglucinol.

All the earlier procedures suffer from limitations including use of a multi-step synthesis, a poor overall yield, or the hazards of preparing very sensitive, highly explosive intermediates during preparation of trinitrophloroglucinol. An alternative process is desirable to allow the improved production of trinitrophloroglucinol.

The novel process of this invention concerns the direct nitration of phloroglucinol and provides a simple, inexpensive and efficient one-pot synthetic route to trinitrophloroglucinol.

Huntress and Mulliken previously reported an undetailed description of the nitration of phloroglucinol to obtain trinitrophloroglucinol in "Identification of Pure Organic Compounds," p. 248, John Wiley and Sons, Inc., New York (1941). This method consisted of adding a solution of 0.1 g of phloroglucinol in concentrated $H_2SO_4$ into a mixture of 1 ml each concentrated $H_2SO_4$ and concentrated $HNO_3$. However, the authors of this specification were unable to duplicate the earlier results. Using that procedure, scale up to even 1 g of phloroglucinol was unsuccessful and no product could be isolated. Accordingly, the hereinafter disclosed method of preparing trinitrophloroglucinol was developed after considerable experimentation.

SUMMARY OF THE INVENTION

The novel process of this invention comprises the steps of cooling a reaction mixture of phloroglucinol and sulphuric acid to 0°–5° C., slowly adding a mixture of nitric acid and sulfuric acid at a rate which maintains the reaction temperature under 8° C., and stirring the reaction mixture until a precipitate is formed.

OBJECTS OF THE INVENTION

Accordingly, it is an object of this invention to provide a new method of making trinitrophloroglucinol.

It is another object of this invention to provide a safe, simple, economical method of making trinitrophloroglucinol.

Still another object of this invention is to provide for the direct nitration of phloroglucinol in a one-pot synthetic route to trinitrophloroglucinol.

These and other objects of the invention will become apparent from the following specification.

DETAILED DESCRIPTION OF THE INVENTION

The present invention concerns a new process for preparing trinitrophloroglucinol in an inexpensive manner by the direct nitration of phloroglucinol. Phloroglucinol is a preferred starting material because of its low price and ready availability. In contrast to the earlier work of Huntress and Mulliken, the present procedure involves changing the order of addition and using a stoichiometric amount of nitric acid and phloroglucinol to achieve excellent results. In the present invention, a nitric acid and sulfuric acid mixture was added to phloroglucinol in sulfuric acid solution.

An excess of nitric acid is to be avoided to properly prepare the trinitrophloroglucinol. Otherwise, the product will be lost through oxidation. The nitration of phloroglucinol must be performed in the minimum amount of time possible. Then, the trinitrophloroglucinol product must be quickly removed from, and washed free of, nitric acid to minimize loss of product to oxidation. This improved procedure has been successfully scaled up to 1 g, 10 g and 25 g of reactant phloroglucinol with yields of trinitrophloroglucinol up to 70%.

The following examples illustrate the present invention. Obviously, modifications and variations are possible in light of the disclosed teachings. It should therefore be understood that the present invention is limited only by the scope of the appended claims.

EXAMPLE 1

A solution of 38 ml of 71% $HNO_3$ (0.608 mole) in 62 ml of 97% $H_2SO_4$ was added to a mechanically stirred solution of 25.22 g (0.2 mole) of phloroglucinol (obtained from Matheson, Coleman and Bell, anhydrous, m.p. 217°–219° C.) in 500 ml of 97% $H_2SO_4$ over a one hour period with ice-bath cooling. During addition the temperature of the reaction mixture is maintained at 5°–8° by adjusting the addition rate to maintain a slightly exothermic reaction. After addition is complete, stirring is continued for 9 minutes. The mixture, containing a precipitate, is then poured over 1800 g of ice. The resulting precipitate is immediately filtered through a coarse sintered-glass funnel by gentle suction and washed with two 125 ml portions of aqueous 3N HCl.

After drying in vacuo at 25° C., 36.56 g (70% yield) of trinitrophloroglucinol is obtained (m.p. 160°–163° C.). The product is quite pure with an IR spectrum identical to high purity trinitrophloroglucinol. It may be recrystallized from 800 ml of hot dichloroethane which affords 25 g (70% recovery) of high purity trinitrophloroglucinol as long spear-like needles (m.p. 164°–165° C.) and three subsequent crops (m.p. 158°–160° C.) for 96% total recovery. An IR (KBr)

spectrum showed bands at 3000 (br s), 1625, 1575, 1515, 1345, 1310, 1200, 1170, 915, 810, 788, 758, and 700 cm$^{-1}$.

Anal. Calcd. for $C_6H_3N_3O_9$ : C, 27.60; H, 1.16; N, 16.09. Found: C, 27.42; H, 1.38; N, 15.86.

EXAMPLE 2

A similar experiment employing 10 g of phloroglucinol, yielded 11.1 g (54%) trinitrophloroglucinol (m.p. 160°–163° C.). Recrystallization from 800 ml of boiling aqueous 3N HCl gave 10.07 g (90% recovery) of high purity product (m.p. 163°–165° C.).

What is claimed is:

1. A method of making trinitrophloroglucinol comprising the steps of:

cooling a reaction mixture of phloroglucinol and sulfuric acid;

slowly adding to said reaction mixture a solution of nitric acid and sulfuric acid at a rate which maintains a reaction temperature of below 8° C.; and stirring said reaction mixture until precipitate of said trinitrophloroglucinol forms.

2. A method of making trinitrophloroglucinol according to claim 1 wherein said nitric acid and said phloroglucinol are present in stoichiometric amounts of 3 moles nitric acid per 1 mole phloroglucinol.

3. A method of making trinitrophloroglucinol according to claim 1 further comprising the step of rapidly isolating said precipitate of trinitrophloroglucinol by pouring said reaction mixture over ice, filtering and washing said precipitate.

4. A method of making trinitrophloroglucinol according to claim 2 further comprising the step of rapidly isolating said precipitate of trinitrophloroglucinol by pouring said reaction mixture over ice, filtering and washing said precipitate.